(12) United States Patent
Ellis

(10) Patent No.: US 7,485,589 B2
(45) Date of Patent: Feb. 3, 2009

(54) CATIONIC FIBROUS SANITIZING SUBSTRATE

(75) Inventor: Dianne Ellis, Cary, NC (US)

(73) Assignee: PGI Polymer, Inc., Charlotte, NC (US)

( * ) Notice: Subject to any disclaimer, the term of this patent is extended or adjusted under 35 U.S.C. 154(b) by 229 days.

(21) Appl. No.: 11/194,939

(22) Filed: Aug. 2, 2005

(65) Prior Publication Data

US 2007/0032151 A1  Feb. 8, 2007

(51) Int. Cl.
*B32B 27/04* (2006.01)

(52) U.S. Cl. .................. 442/123; 442/408; 442/327

(58) Field of Classification Search ............. 442/123, 442/124, 408; 424/414
See application file for complete search history.

(56) References Cited

U.S. PATENT DOCUMENTS

| | | | |
|---|---|---|---|
| 3,485,706 A | 12/1969 | Evans | |
| 4,536,361 A | 8/1985 | Torobin et al. | |
| 5,098,764 A | 3/1992 | Drelich | |
| 5,718,972 A | 2/1998 | Murase et al. | |
| 5,970,583 A | 10/1999 | Groten et al. | |
| 6,114,017 A | 9/2000 | Fabbricante et al. | |
| 6,324,738 B1 | 12/2001 | Fleissner | |
| 6,460,233 B2 | 10/2002 | Noelle | |
| 6,734,157 B2 * | 5/2004 | Radwanski et al. | 510/439 |
| 2005/0155631 A1 * | 7/2005 | Kilkenny et al. | 134/6 |

OTHER PUBLICATIONS

Pourjavadi, A., et al., "Superabsorbency, pH-Sensitivity and Swelling Kinetics of Partially Hydrolyzed Chitosan-g-poly (Acrylamide)," 30, 2006 (no month), 595-608, Received Feb. 1, 2006, Tubitak, as a printout of: http://journals.tubitak.gov.tr/chem/issues/kim-06-30-5/kim-30-5-7-0602-3, Aug. 3, 2007.
PCT International Search Report, Int'l Appln. No. PCT/US06/29967, Oct. 31, 2007, 2 pages.
PCT Written Opinion Of The International Searching Authority, Int'l Appln. No. PCT/US06/29967, Oct. 31, 2007, 5 pages.

* cited by examiner

*Primary Examiner*—Arti Singh
(74) *Attorney, Agent, or Firm*—Kilyk & Bowersox, PLLC; Valerie Calloway

(57) ABSTRACT

The present invention is directed to an essentially binder free cleaning and/or sanitizing nonwoven article including a cationic fibrous component for cleaning a surface, to be utilized with a sanitizing solution without depleting the solution's effectiveness. The cationic cleaning or sanitizing article of the present invention is particularly engineered to be stored in a quaternary amine sanitizing solution over an extended period of time while maintaining at least the minimum required FDA ppm of the sanitizing solution.

19 Claims, No Drawings

CATIONIC FIBROUS SANITIZING SUBSTRATE

TECHNICAL BACKGROUND

The present invention generally relates to an article for cleaning and/or sanitizing a surface, and more specifically relates to an essentially binder free nonwoven cleaning and/or sanitizing article including a cationic fibrous component to be utilized with a sanitizing solution without depleting the solution's effectiveness.

BACKGROUND OF THE INVENTION

Over the years, the use of disposable substrates in cleaning applications has been well practiced. Suitable substrates have included woven and nonwoven fabrics, and various combinations thereof. Further, such substrates have been impregnated with cleaning agents such as disinfectants, solvents, anti-microbials, detergents, and other chaotropes. The resulting cleaning products fabricated from such impregnated substrates have found acceptance with the general public as a convenient and practical means for the cleaning of surfaces. In particular, such constructs have been successful in the consumer wipes markets as external surface cleaning and/or sanitizing articles or wipes.

Nonwoven surface cleaning or sanitizing articles fabricated for the food service or hospitality industry ordinarily include a fibrous blend of polyester and rayon, as well as a binder formulation. Such sanitizing articles have gained popularity over the years versus woven terry towels, due to the benefits derived from with utilizing a limited or single use nonwoven sanitizing or cleaning article. Reusable damp woven terry cloth towels are thought to be more susceptible to bacterial build up as they are left standing between uses. It is also thought that repeatedly using a standing damp towel to wipe down a food prep surface may actually be re-introducing harmful bacteria into the food preparation area.

The Federal Food and Drug Administration has implemented food code 3-304.14B2, which states, "cloths used for wiping food spills shall be wet and cleaned as specified under 4-802.11(D), stored in a chemical sanitizer at a concentration specified in 4-501.114, and used for wiping spills from food-contact and non-food contact surfaces of equipment. This requires a solution that can be prepared and maintained at a concentration level to satisfy not only the FDA standard, but also any additional state or local regulations that may apply."

As the use of nonwoven sanitizing articles or wipes in the food service industry has increased, nonwoven fabrics have been engineered that facilitate the sanitizing process of preparation and serving surfaces. In spite of these developments, it has been found that certain nonwoven fabrics have a detrimental effect on a sanitizing solution, wherein the inherent or applied ionic properties of the sanitizing and/or cleaning article neutralize the effectiveness of the sanitizing solution over time. In light of such findings, there remains a need for a nonwoven external surface cleaning and/or sanitizing article suitable for the food service and hospitality industry that may be used in conjunction with a quaternary amine sanitizing solution without depleting the level of effectiveness of the solution over a given period of time.

SUMMARY OF THE INVENTION

The present invention is directed to an essentially binder free cleaning and/or sanitizing nonwoven article including a cationic fibrous component for cleaning a surface to be utilized with a sanitizing solution without depleting the solution's effectiveness. FDA regulations require wet cleaning and sanitizing articles to be stored in a sanitizing solution with a specific effective ppm between uses. Accordingly, the cationic cleaning or sanitizing article of the present invention is particularly engineered to be stored in a quaternary amine sanitizing solution over an extended period of time while maintaining at least the minimum required FDA ppm of the sanitizing solution.

The cleaning or sanitizing article of the present invention includes a nonwoven substrate with a cationic fibrous component, such as a chitosan fiber or alternate fiber with a cationic finish, for use in conjunction with the quaternary amine sanitizing solution. The cleaning or sanitizing article is particularly useful in the food service industry to wipe external surfaces, including, but not limited to food preparation surfaces, dining surfaces, equipment surfaces, kitchen surfaces, and bathroom surfaces.

In one embodiment, the cleaning or sanitizing article is a single layer nonwoven fibrous substrate, wherein the substrate includes a hydroentangled blend of carded polyester, rayon, and chitosan staple fiber. The sanitizing article of the present invention may include two or more layers. Suitable layers include additional nonwoven layers, such as carded staple fiber layers, continuous or discontinuous filament layers, airlaid and wetlaid fiber layers, thermally bonded layers, spunlace layers, and combinations thereof, as well as film layers.

In another embodiment, the cleaning or sanitizing article may include two or more layers that impart a dual performance characteristics to the article. In such an embodiment, the article includes a cationic fibrous component and has at least one face or side for applying the sanitizing solution to an external surface and maintaining the concentration level of a quaternary amine sanitizer at an effective level when stored in the sanitizer for an extended period of time. The article may further include a dissimilar opposing side, wherein the opposing side may be imparted with a degree of abrasiveness for enhancing the removal of particulate matter.

It is within the purview of the present invention to incorporate the cationic component into the cleaning or sanitizing article as a fibrous component, wherein the cationic fibrous component is an intimate part of the fibrous composition. The sanitizing article may include 100% cationic fiber or the cationic fiber may be blended in part with one or more additional natural and/or synthetic fibers. Further, the cleaning or sanitizing article including the cationic fibrous component maintains the effectiveness level of the quaternary amine sanitizing solution, wherein the quaternary amine solution remains at least 90% effective after one hour of repeated use with the cationic cleaning or sanitizing article of the present invention.

Other features and advantages of the present invention will become readily apparent from the following detailed description and the appended claims.

DETAILED DESCRIPTION

While the present invention is susceptible of embodiment in various forms, there is shown in the drawing, and will hereinafter be described, a presently preferred embodiment, with the understanding that the present disclosure is to be considered as an exemplification of the invention, and is not intended to limit the invention to the specific embodiment illustrated.

The cleaning or sanitizing article of the present invention includes a nonwoven substrate with a cationic fibrous component for use in conjunction with a quaternary amine sanitizing solution. The sanitizing article contains a cationic charge that is imparted by the fibrous components of the article and is further essentially free of any binder formulations. Additionally, the cationic cleaning or sanitizing article is particularly suited for use and storage between uses in a quaternary amine solution, wherein the solution maintains at least 90% of the quaternary amine after one hour of use with the article of the present invention.

According to the present invention, the cationic fibrous component of the sanitizing article may include a chitosan fibrous component, an alternate fiber including a cationic finish, or a combination of cationic fiber. Chitosan fiber is an exemplary cationic fiber commercially available under the trade name CRABYON®, made available by Omikenshi Co., Ltd. of Japan. The chitosan component of the present invention may also be topically applied as a coating on the sanitizing article. Chitosan is the commonly used name for poly-[1-4]-β-D-glucosamine. Chitosan is chemically derived from chitin, which is a poly-[1-4]-β-D-glucosamine, which, in turn, is derived from the cell walls of fungi, the shells of insects and, especially, crustaceans. Insects, yeast, mushroom cell walls, and certain bacterial cell walls also contain chitin, but these sources have not been commercialized or studied to the same degree as seafood chitin. Chitosan is also generally soluble in various organic acids and is available in aqueous or non-aqueous forms. A chitosan compound or solution may optionally be topically applied to the cleaning or sanitizing article by one or more methods known in the art, including submerging, padding, kiss coatings, or spraying.

The cleaning or sanitizing article includes a nonwoven substrate, wherein the nonwoven substrate typically further includes a fibrous batt incorporating between about 3%-100% by weight cationic fiber and more preferably between about 5%-60% by weight cationic fiber. In accordance with the present invention, the sanitizing article is typically essentially free of any binder systems, and capable of maintaining the effectiveness of a quaternary amine sanitizing solution. Table 1 includes three suitable embodiments of a cleaning or sanitizing articles made in accordance with the principles of the present invention, labeled as A, B, and C.

As illustrated in embodiment A of Table 1, the cleaning or sanitizing article of the present invention is capable of retaining at least 90% of the dual quaternary amine effective ppm (parts per million) present in the initial sanitizing solution (shown as 0 hours in the Tables) after one hour of use with the sanitizing article. Further, embodiments B and C of Table 1 show at least a 95% ppm effectiveness level of the dual quaternary sanitizing solution after one hour of use with the sanitizing article. Table 2 is illustrative of a comparative sanitizing article without a cationic fibrous component. As can be seen, after one hour of use in a quaternary amine sanitizing solution, the effective ppm of quaternary amine has dropped below 90%.

The cleaning or sanitizing article made in accordance with the present invention includes a nonwoven substrate incorporating a cationic component, wherein the sanitizing article has at least one face or side for applying the sanitizing solution to an external surface, while maintaining the concentration level of the sanitizer at an effective level. The nonwoven layer may include a single layer or two or more layers, including, but not limited to a carded layers, airlaid layers, wetlaid layers, spunlace layers, filamentary layers, coforms, films, or a combination thereof. Filamentary layers may include spunbond or meltblown webs, wherein the web may further include nano-denier fibers. Nano-denier fibers are disclosed in U.S. Pat. No. 4,536,361 issued on Nov. 16, 1982 to inventor Torobin, U.S. Pat. No. 6,114,017 issued on Jul. 23, 1997 to inventor Fabbricante, et al., as well as U.S. Pat. No. 5,718,972 issued on Feb. 7, 1996 to inventor Murase, et al. and U.S. Pat. No. 5,970,583 issued on Jan. 5, 1999 to inventor Groten, et al., all hereby incorporated by reference as set forth fully herein. Filamentary laminates may also be utilized in whole or in part of the nonwoven substrate, such as SS (spunbond spunbond), SMS (spunbond meltblown spunbond, SMMS (spunbond meltblown meltblown spunbond), SMSM (spunbond meltblown spunond meltblown), and the like.

In one embodiment, the cleaning or sanitizing article may include two or more layers that impart a dual performance characteristics to the sanitizing article. In such an embodiment, the article including a cationic component has a first face for applying the sanitizing solution to an external surface and a dissimilar opposing second face for providing a function dissimilar to the first face, wherein the opposing second face may be configured to exhibit abrasiveness for enhancing the removal of particulate matter.

In accordance with the present invention, the sanitizing article may further include natural fiber, synthetic fiber, and the combinations thereof. Suitable natural fibers include, but are not limited to rayon, wood pulp, wool, silk, jute, hemp, linen, sisal, and combinations thereof. Synthetic fibers that may be used in accordance with the present invention include those formed from polymers chosen from the group of thermoplastic polymers consisting of polyolefins, polyamides, and polyesters, wherein the polyolefins are chosen from the group consisting of polypropylene, polyethylene, and combinations and modifications thereof. Optionally, the one or more layers of the sanitizing article may include one or more additives, such as fragrances, pigments, dyes, surfactants, and skin enhancing conditioners, including emollients, lipids, and natural botanicals.

The nonwoven substrate and layers thereof may be bonded by various techniques known in art which are not meant to be a limiting factor of the present invention. The substrate may be mechanically or chemically bonded. Mechanical bonding techniques include hydroentanglement, needle-punching, calendaring, through-air bonding, ultrasonic bonding, and high pressure bonding. Further, filamentary layer and film layers may be optionally directly extruded onto the nonwoven substrate.

In addition, the cleaning or sanitizing article may further include one or more raised profiled elements and/or apertures. Raised profiled elements may be imparted into the nonwoven layer by embossing the layer, or effected by hydraulic energy upon a foraminous surface, such as a wire screen, a metal perforated drum, a three-dimensional belt, or image transfer device. Exemplary foraminous surfaces are taught in U.S. Pat. No. 3,485,706 issued on Jan. 18, 1968 to inventor Evans, U.S. Pat. No. 6,324,738 issued on Nov. 16, 1999 to inventor Fleissner, U.S. Pat. No. 6,460,233 issued on Jan. 9, 2001 to inventor Noelle, and U.S. Pat. No. 5,098,764 issued on Mar. 12, 1990 to inventor Drelich, et al., which are hereby incorporated by reference as if set forth fully herein.

According to the present invention an article for cleaning or sanitizing a surface including a cationic fibrous component prolongs the usefulness of the quaternary amine sanitizing solution over an extended period of time. The sanitizing article further improves the sanitation performance of the quaternary amine solution without requiring the use of a binder system to prevent the article from deleteriously neutralizing the effectiveness of the quaternary amine solution. The sanitizing article may include one or more layers selected to benefit the overall cleaning performance of the article and may be treated with one or more post-treatments to further enhance aesthetic or physical characteristics of the sanitizing article.

From the foregoing, it will be observed that numerous modifications and variations can be affected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

TABLE 1

|  | 0 hr. | 1 hr |
|---|---|---|
| Control (no towels) | 211.4 | 210.6 |
| A: 5% Chitosan fiber/40% PET/55% rayon, no binder | 203.5 | 189.9 |
| B: 10% Chitosan fiber/40% PET/50% rayon, no binder | 205.5 | 198.2 |
| C: 15% Chitosan fiber/40% PET/45% rayon, no binder | 201.1 | 197.6 |

TABLE 2

|  | 0 hr. | 1 hr |
|---|---|---|
| Control (no towels) | 206.9 | 206.9 |
| 35% rayon/35% Tencel/30% PET (no binder) | 150.9 | 127.4 |

What is claimed is:

1. A sanitizing article, comprising:
a nonwoven substrate, including
a cationic fibrous component comprising poly-[1-4]-β-D-glucosamine fiber disposed within the nonwoven substrate, wherein said sanitizing article comprises about 3%-100% by weight poly-[1-4]-β-D-glucosamine fiber, wherein the sanitizing article stores in a sanitizing solution containing quaternary amine such that at least 90% of said quaternary amine in ppm is maintained in said sanitizing solution compared to an initial solution thereof after one hour storage in said sanitizing solution.

2. A sanitizing article as in claim 1, wherein the sanitizing article comprises about 5%-60% by weight poly-[1-4]-β-D-glucosamine fiber.

3. A sanitizing article as in claim 1, wherein the sanitizing article comprises two or more layers.

4. A sanitizing article as in claim 3, wherein the layers are selected from the group consisting of carded layers, airlaid layers, wetlaid layers, spunlace layers, filamentary layers, coforms, films, and combinations thereof.

5. A sanitizing article as in claim 4, wherein the filamentary layers are selected from the group consisting of spunbond layers, meltblown, layers, and combinations thereof.

6. A sanitizing article as in claim 4, wherein the filamentary layers are nano-denier filamentary layers.

7. A sanitizing article as in claim 1, wherein the nonwoven substrate is selected from the group consisting of natural fibers, synthetic fibers, and the combinations thereof.

8. A sanitizing article as in claim 1, wherein said nonwoven substrate is a hydroentangled nonwoven fibrous blend comprising polyester fibers, rayon fibers, and 5 to 15% poly-[1-4]-β-D-glucosamine staple fibers, wherein said sanitizing article is essentially free of binder.

9. A sanitizing article as in claim 1, wherein the sanitizing article stores in a sanitizing solution containing quaternary amine such that at least 95% of said quaternary amine in ppm is maintained in said sanitizing solution compared to an initial solution thereof after one hour storage in said sanitizing solution.

10. A method for making a sanitizing article, the method comprising the steps of: forming a fibrous batt, wherein a cationic fibrous component comprising poly-[1-4]-β-D-glucosamine fiber is disposed within the fibrous batt; and consolidating the fibrous batt into a nonwoven substrate to provide a sanitizing article comprising about 3%-100% by weight poly-[1-4]-β-D-glucosamine fiber, wherein the sanitizing article stores in a sanitizing solution containing quaternary amine such that at least 90% of said quaternary amine in ppm is maintained in said sanitizing solution compared to an initial solution thereof after one hour storage in said sanitizing solution.

11. A method for making a sanitizing article as in claim 10, further comprising storing said nonwoven substrate in quaternary amine solution.

12. An article for sanitizing a surface utilizing a sanitizing solution comprising: a nonwoven substrate, including a cationic fibrous component comprising poly-[1-4]-β-D-glucosamine fiber disposed within the nonwoven substrate, wherein said article comprises about 3%-100% by weight poly-[1-4]-β-D-glucosamine fiber, and wherein the article has at least one face for applying sanitizing solution to an external surface, wherein the article stores in a sanitizing solution containing quaternary amine such that at least 90% of said quaternary amine in ppm is maintained in said sanitizing solution compared to an initial solution thereof after one hour storage in said sanitizing solution.

13. An article for sanitizing a surface utilizing a sanitizing solution as in claim 12, further comprising a quaternary amine solution in which the nonwoven substrate is stored.

14. An article for sanitizing a surface utilizing a sanitizing solution as in claim 13, wherein the article stores in a sanitizing solution containing quaternary amine such that at least 95% of said quaternary amine in ppm is maintained in said sanitizing solution compared to an initial solution thereof after one hour storage in said sanitizing solution.

15. An article for sanitizing a surface utilizing a sanitizing solution as in claim 12, wherein the article further comprises a first face for applying the sanitizing solution to an external surface and a dissimilar opposing second face for providing a function dissimilar to the first face.

16. An article for sanitizing a surface utilizing a sanitizing solution as in claim 15, wherein the second face enhances the removal of particulate matter from an external surface.

17. A sanitizing article as in claim 1, wherein the sanitizing article contains cationic charge imparted by fibrous components of said article and is essentially free of binder.

18. A method for making a sanitizing article as in claim 10, wherein the sanitizing article contains cationic charge imparted by fibrous components of said article and is essentially free of binder.

19. An article for sanitizing a surface utilizing a sanitizing solution as in claim 12, wherein the article contains cationic charge imparted by fibrous components of said article and is essentially free of binder.

* * * * *